US007166294B2

(12) United States Patent
Maupin et al.

(10) Patent No.: US 7,166,294 B2
(45) Date of Patent: Jan. 23, 2007

(54) CONTROL OF ARTHROPODS IN RODENTS

(75) Inventors: Gary O. Maupin, Fort Collins, CO (US); Marc C. Dolan, Fort Collins, CO (US); Patrick D. Lowder, Pinehurst, NC (US)

(73) Assignees: Centers for Disease Control and Prevention, Atlanta, GA (US); Aventis CropScience S.A., Lyons (FR)

( * ) Notice: Subject to any disclaimer, the term of this patent is extended or adjusted under 35 U.S.C. 154(b) by 30 days.

(21) Appl. No.: 10/282,984

(22) Filed: Oct. 28, 2002

(65) Prior Publication Data
US 2003/0134877 A1 Jul. 17, 2003

Related U.S. Application Data

(63) Continuation of application No. 09/595,177, filed on Jun. 16, 2000, now abandoned.

(51) Int. Cl.
*A01N 43/56* (2006.01)
*A01N 25/32* (2006.01)
(52) U.S. Cl. .................. 424/406; 43/131; 119/664; 424/405; 424/409; 424/441; 424/84; 514/406; 514/407
(58) Field of Classification Search .......... 424/405, 424/407, 409, 84, 411; 42/131, 114; 514/407, 514/406; 119/339, 650, 652, 656, 660, 664, 119/672; 43/131
See application file for complete search history.

(56) References Cited

U.S. PATENT DOCUMENTS

| | | | |
|---|---|---|---|
| 416,951 A | 12/1889 | Roop | 119/673 |
| 1,569,904 A | 1/1926 | Wright | 119/652 |
| 1,582,144 A | 4/1926 | Pflaum | 119/652 |
| 2,316,932 A | 4/1943 | Bruce | 119/159 |
| 2,925,065 A | 2/1960 | Worden | 119/157 |
| 3,902,461 A | 9/1975 | Cortner | 119/159 |
| 4,074,659 A | 2/1978 | Mowbray et al. | 119/159 |
| 4,281,471 A | 8/1981 | Jenkins et al. | 43/131 |
| 4,324,202 A | 4/1982 | Stonestreet et al. | 119/51 |
| 4,662,104 A | 5/1987 | Mather et al. | 43/132.1 |
| 4,753,032 A | 6/1988 | Sherman | 43/131 |
| 5,027,747 A | 7/1991 | Talley | 119/157 |
| 5,232,940 A | 8/1993 | Hatton et al. | 514/407 |
| 5,272,832 A | 12/1993 | Marshall et al. | 43/131 |
| 5,367,983 A | 11/1994 | Pound et al. | 119/53 |
| 5,447,122 A | 9/1995 | Cortner | 119/159 |
| 5,448,852 A | 9/1995 | Spragins et al. | 43/131 |
| 5,806,237 A | 9/1998 | Nelson et al. | 43/131 |
| 5,932,437 A | 8/1999 | Poche | 435/32 |
| 5,983,558 A | 11/1999 | Las et al. | 43/131 |
| 6,162,820 A | 12/2000 | Jeannin et al. | 514/407 |
| 6,395,765 B1 | 5/2002 | Etchegaray | 514/407 |

FOREIGN PATENT DOCUMENTS

| | | |
|---|---|---|
| EP | 0 295 117 | 12/1988 |
| WO | WO 97/12521 | 4/1997 |
| WO | 98/02042 | 1/1998 |
| WO | WO 98/42191 | 10/1998 |

OTHER PUBLICATIONS

Copies of Slides presented at oral presentations by inventors or their assistants prior to Jun. 16, 1999.
Cover page and pp. 1, 5 and 16 of booklet prepared by American Lyme Disease Foundation, Inc. including abstract of presentation given by inventor Gary O. Maupin on Mar. 8, 1999 (date of booklet unknown).
Gage et al., Flea (Siphonaptera: Ceratophyllidae, Hystrichopsyllidae) and Tick (Acarina:Ixodidae) Control on Wood Rats Using Host-Targeted Liquid Permethrin in Bait Tubes; J. Med. Entomol., pp. 46-51, vol. 34, No. 1, (Jan. 1997).
Lane et al., Modified bait tube controls disease-carrying ticks and fleas; California Agriculture; vol. 52, No. 2, cover page and pp. 3, 43-48 (Mar.-Apr. 1998).
Barnes; Surveillance and Control of Bubonic Plague in the United States; Symp. Zool. Soc. Lond., No. 50, 237-270 (1982).
Kartman; An Insecticide-Bait Box Method for Plague Control in Certain Areas of the Pacific Region; Proceedings of the Ninth Pacific Science Congress, vol. 19, pp. 49-52 (1957).
Sonenshine and Haines, A Convenient Method for Controlling Populations of the American Dog Tick, Dermacentor Variabilis (Acari:Ixodidae), In the Natural Environment, J. Med. Entomol., vol. 22, No. 5, pp. 577-583 (Sep. 1985).
Kartman; Further Observations on an Insecticide-bait-box Method for the Control of Sylvatic Plague Vectors: Effect of Prolonged Field Exposure to DDT Powder; J. Hyg., Camb., vol. 58, pp. 119-124 (1960).
Kartman; An Insecticide-Bait-Box Method for the Control of Sylvatic Plague Vectors; J. Hyg., vol. LVI, pp. 455-465 (1958).
Barnes and Kartman; Control of Plague Vectors on Diurnal Rodents in the Sierra Nevada of California by Use of Insecticide Bait-Boxes; J. Hyg., Camb., vol. 58, pp. 347-355 (1960).
Morris, K. D., Proctor, R.D., and Kaukeinen, D.E., "Design and Evaluation Criteria for Development of Toxic Wicks for Rodent Control," *Vertebrate Pest Control and Management Materials: Fourth Symposium. ASTM STP 817*, D.E. Kaukeinen, Ed., American Society for Testing and Materials, Philadelphia, 1983, pp. 165-182.
Maupin et al., "Laboratory and Field Evaluation of Rodent-targeted Acaricides for Controlling *Ixodes* ssp", poster presentation of VII International Conference on Lyme Borreliosis and Other Emerging Tick-Borne Diseases, Munich, Germany, presented Jun. 22, 1999.
U.S. Appl. No. 09/595,035, filed Jun. 16, 2000, Maupin, et al., "Control of Arthropod Vectors of Parasitic Diseases".
U.S. Appl. No. 09/595,034, filed Jun. 16, 2000, Maupin, et al., "Apparatus for Applying Chemicals to Rodents,".
Maupin, G. et al., "The MaxForce® Tick Managment System™ and its Role in Reducing the Incidence of Lyme Disease", National Conference on Urban Entomology, 2004.

*Primary Examiner*—Neil S. Levy
(74) *Attorney, Agent, or Firm*—Connolly Bove Lodge and Hutz LLP

(57) ABSTRACT

The present invention provides a method for controlling ectoparasites of small rodents, thereby preventing the transmission of diseases by arthropod vectors.

22 Claims, No Drawings

CONTROL OF ARTHROPODS IN RODENTS

CROSS-REFERENCE TO RELATED APPLICATION

The present application is a continuation of U.S. patent application Ser. No. 09/595,177, which was filed on Jun. 16, 2000, in the names of Gary O. Maupin, Marc C. Dolan and Patrick D. Lowder.

FIELD OF THE INVENTION

The present invention relates to a method of controlling ectoparasitic vectors of diseases, particularly bacterial or viral diseases.

BACKGROUND OF THE INVENTION

Lyme disease was first recognized in the United States in 1975, after a mysterious outbreak of arthritis near Lyme, Conn. Since then, reports of Lyme disease have increased dramatically, and the disease has become an important public health problem in some areas of the United States. Lyme disease is an infection caused by *Borrelia burgdoferi*, a member of the family of spirochetes, or corkscrew-shaped bacteria.

Lyme disease is spread by the bite of ticks of the genus *Ixodes* that are infected with *Borrelia burgdorferi*. The deer (or bear) tick, *Ixodes scapularis*, which normally feeds on the white-footed mouse, the white-tailed deer, other mammals, and birds, is responsible for transmitting Lyme disease bacteria to humans in the northeastern and north-central United States. In these regions, this tick is also responsible for the spreading of babesiosis, a disease caused by a malaria-like parasite. On the Pacific Coast, the bacteria are transmitted to humans by the western black-legged tick, *I. pacificus*. Another newly recognized and serious disease that is transmitted by both *I. scapularis* and *I. pacificus* is human granulocytic ehrlichiosis, the pathogen of which is a rickettsial bacterium.

*Ixodes* ticks are much smaller than common dog and cattle ticks. In their larval and nymphal stages, they are no bigger than a pinhead. Adult ticks are slightly larger. Ticks can attach to any part of the human body but often attach to the more hidden and hairy areas such as the groin, armpits, and scalp. Research in the eastern United States has indicated that, for the most part, ticks transmit Lyme disease to humans during the nymphal stage, probably because nymphs are more likely to feed on a person and are rarely noticed because of their small size (less than two mm). Thus, the nymphs typically have ample time to feed and transmit the infection since ticks are most likely to transmit infection after approximately two or more days of feeding.

Tick larvae are smaller than the nymphs, but they rarely carry the infection at the time of feeding and are probably not important in the transmission of Lyme disease to humans.

Adult ticks can transmit the disease, but since they are larger and more likely to be removed from a person's body within a few hours, they are less likely than the nymphs to have sufficient time to transmit the infection. Moreover, adult *Ixodes* ticks are most active during the cooler months of the year, when outdoor activity is limited. Adults quest for hosts on grasses, shrubs and brush at heights of up to one meter. Immature *Ixodes* search for host animals from the tips of grasses and shrubs (not from trees) and leaf litter near the ground and transfer to animals or persons that brush against these substrates. Ticks only crawl; they do not fly or jump. Ticks found on the scalp usually have crawled there from lower parts of the body. Ticks feed on blood by inserting their mouth parts (not their whole bodies) into the skin of a host animal. They are slow feeders: a complete blood meal can take several days. As they feed, their bodies slowly enlarge.

Although in theory Lyme disease could spread through blood transfusions or other contact with infected blood or urine, no such transmission has been documented. There is no evidence that a person can get Lyme disease from the air, food or water, from sexual contact, or directly from wild or domestic animals. There is no convincing evidence that Lyme disease can be transmitted by insects such as mosquitoes, flies, or fleas. Campers, hikers, outdoor workers, and others who frequent wooded, brushy, and grassy places are commonly exposed to ticks, and this may be important in the transmission of Lyme disease in some areas. Because new homes are often built in wooded areas, transmission of Lyme disease near homes has become an important problem in some areas of the United States. The risk of exposure to ticks is greatest in the woods and garden fringe areas of properties, but ticks may also be carried by animals into lawns and gardens.

Geographic distribution of Lyme disease is wide in northern temperate regions of the world. In the United States, the highest incidence occurs in the Northeast, from Massachusetts to Maryland. Incidence is also notable in the North-central states, especially Wisconsin and Minnesota, and the West Coast, particularly northern California. For Lyme disease to exist in an area, at least three closely interrelated elements must be present in nature: the Lyme disease bacteria, ticks that can transmit them, and mammals (such as mice and deer) to provide food for the ticks in their various life stages. Ticks that transmit Lyme disease can be found in temperate regions that may have periods of very low or high temperature and a constant high relative humidity at ground level. Knowing the complex life cycle of the ticks that transmit Lyme disease is important in understanding the risk of acquiring the disease and in finding ways to prevent it: The life cycle of these ticks requires two years to complete. Adult ticks feed and mate on large animals, especially deer, in the fall and early spring. Female ticks then drop off these animals to lay eggs on the ground. By summer, eggs hatch into larvae. Larvae feed on mice and other small mammals and birds in the summer and early fall and then are inactive until the next spring when they molt into nymphs. Nymphs feed on small rodents and other small mammals and birds in the late spring and summer and molt into adults in the fall, completing the 2-year life cycle. Larvae and nymphs typically become infected with Lyme disease bacteria when they feed on infected small animals, particularly the white-footed mouse. The bacteria remain in the tick as it changes from larva to nymph or from nymph to adult. Infected nymphs and adult ticks then bite and transmit Lyme disease bacteria to other small rodents, other animals, and humans, all in the course of their normal feeding behavior. Lyme disease in domestic animals Domestic animals may become infected with Lyme disease bacteria and some of these (dogs, for instance) may develop arthritis. Domestic animals can carry infected ticks into areas where humans live, but whether pet owners are more likely than others to get Lyme disease is unknown.

There are proposed solutions to the prevention of transmission of tick-borne parasites to humans. For example, U.S. Pat. Nos. 5,648,398, 5,346,922, and 5,227,406 describe insect repellent compositions which are claimed to repel ticks. However, the use a repellent does not eliminate the vector itself but serves as a "chemical shield" against the ticks so that they will have to find another mammalian host. There are generally no known solutions to arrest the spread of Lyme disease and/or other diseases spread by ticks.

SUMMARY OF THE INVENTION

An object of the present invention is to provide a method of controlling ticks in non-domestic mammals.

Another object of present invention is to provide a method of preventing the transmission of diseases by arthropod vectors.

These and other objects are met in whole or in part by the present invention.

DETAILED DESCRIPTION OF THE INVENTION

The present invention provides a method of controlling ectoparasites of small rodents comprising providing one or more enclosures of appropriate size to such rodents, the enclosures having one or more peripheral openings allowing entry and egress of rodents, the enclosure including at least one applicator arranged to contact a rodent; providing a composition comprising an ectoparasiticide on the applicator; and placing one or more enclosures in a locus where the rodents are expected, wherein the applicator is arranged and the composition is provided to apply an effective amount of the composition to the skin or hair of the rodent upon contact with the applicator.

The method of the present invention is useful for the control of arthropods that are vectors of diseases such as Lyme disease, Rocky Mountain Spotted Fever, Ehrlichiosis or Babesiosis. In particular, the present invention is useful for control of ticks of the genus *Ixodes*, including *I. scapularis*, *I. pacificus*, *I. spinipalpis*, *Dermacentor variabilis* and *D. andersoni*. The present invention is effective in arresting the transmission of an infective agent such as *Borrelia burgdorferi* from the treated rodent to another mammal such as a deer, mouse, chipmunk or human. In a preferred embodiment the treated rodent is a mouse (e.g., *Peromyscus* spp.) especially the white-footed mouse, *P. leocopus*, rat (e.g., *Rattus* spp. or *Neotoma* spp.), chipmunk (e.g., *Tamias* spp.), vole (e.g., *Microtus* spp.) or squirrel (e.g., *Sciurus* spp., *Tamiasciurus* spp. or *Spermophilus* spp).

Ectoparasiticides are known to those of ordinary skill in the art and are commercially available. A preferred ectoparasiticide according to the present invention is a compound of formula (I):

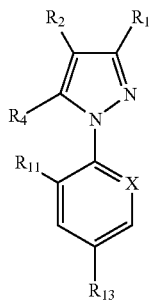

(I)

wherein:

$R_1$ is cyano, acetyl, $C(S)NH_2$, alkyl, haloalkyl, $C(=NOH)NH_2$ or $C(=NNH_2)NH_2$;

$R_2$ is $S(O)_nR_3$; $C_2-C_3$ alkenyl, $C_2-C_3$ haloalkenyl, cycloalkyl, halocycloalkyl or $C_2-C_3$ alkynyl;

$R_3$ is alkyl or haloalkyl;

$R_4$ is $-N=C(R_5)-Z-R_6$, $-N=C(R_5)-N(R_7)-R_8$, or $-N(R_9)-C(R_5)=NR_6$;

$R_5$ is hydrogen; alkyl; or alkyl substituted by halogen, alkoxy, haloalkoxy or $-S(O)mR_{15}$;

$R_6$ and $R_7$ each independently represent hydrogen, alkyl, $C_3-C_5$ alkenyl or $C_3-C_5$ alkynyl; or alkyl substituted by one or more halogen, alkoxy, haloalkoxy, amino, alkylamino, dialkylamino, cyano or $-S(O)_mR_{15}$; or alkyl substituted by phenyl or pyridyl each of which is optionally substituted with one or more groups selected from halogen, nitro and alkyl; or $R_6$ and $R_7$ may form together with the nitrogen to which they are attached a 3 to 7 membered ring which may additionally contain one or more heteroatoms selected from oxygen, nitrogen or sulfur;

$R_8$ is alkoxy, haloalkoxy, amino, alkylamino, dialkylamino, $R_{14}CO-$ or $-S(O)_tR_{10}$;

$R_9$, $R_{10}$ and $R_{14}$ are alkyl or haloalkyl;

$R_{11}$ and $R_{12}$ are independently selected from halogen, hydrogen, CN and $NO_2$;

$R_{13}$ is selected from halogen, haloalkyl, haloalkoxy, $-S(O)_qCF_3$, and $-SF_5$;

$R_{15}$ is alkyl or haloalkyl;

X is selected from nitrogen and $C-R_{12}$;

Z is O, $S(O)_a$; or $NR_7$;

a, m, n and q are independently selected from 0, 1, and 2; and t is 0 or 2; and veterinarily acceptable salts thereof.

Another preferred ectoparasiticide according to the present invention is a compound of formula (XX):

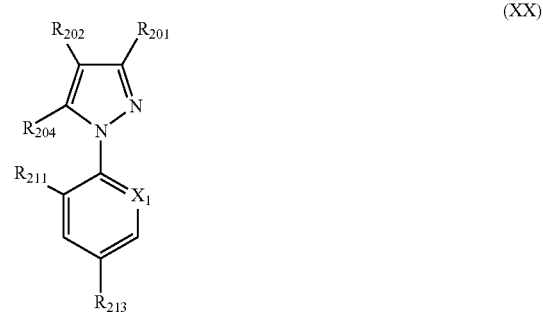

(XX)

wherein:

$R_{201}$ is cyano, C(O)alkyl, $C(S)NH_2$, alkyl, $C(=NOH)NH_2$ or $C(=NNH_2)NH_2$;

$R_{202}$ is $S(O)_hR_{203}$, $C_2-C_3$ alkenyl, $C_2-C_3$ haloalkenyl, cycloalkyl, halocycloalkyl or $C_2-C_3$ alkynyl;

$R_{203}$ is alkyl or haloalkyl;

$R_{204}$ is $-N(R_{205})C(O)CR_{206}R_{207}R_{208}$, $-N(R_{205})C(O)$aryl, or $-N(R_{205})C(O)OR_{207}$;

$R_{205}$ is alkyl, haloalkyl, cycloalkyl, halocycloalkyl, cycloalkylalkyl, halocycloalkylalkyl, alkoxyalkyl, haloalkoxyalkyl, $C_3-C_5$ alkenyl, $C_3-C_5$ haloalkenyl, $C_3-C_5$ alkynyl, $C_3-C_5$ haloalkynyl;

$R_{206}$ is hydrogen, halogen, alkoxy, haloalkoxy, alkoxyalkyl, haloalkoxyalkyl, formyloxy, alkylcarbonyloxy, haloalkylcarbonyloxy, alkylthio, haloalkylthio, alkylsulfinyl, haloalkylsulfinyl, alkylsulfonyl, haloalkylsulfonyl, alkylamino, dialkylamino, haloalkylamino, di(haloalkyl)amino, cycloalkyloxy, halocycloalkyloxy, alkoxyalkoxy, haloalkoxyalkoxy, alkoxyalkoxyalkoxy, aryloxy, or arylalkoxy;

$R_{207}$ and $R_{208}$ are independently hydrogen, alkyl, haloalkyl, cycloalkyl, or halocycloalkyl; or $R_{207}$ and $R_{208}$ may form together with the carbon to which they are attached a 3 to 7 membered ring which additionally may contain one or more heteroatoms selected from nitrogen, oxygen and sulfur;

$X_1$ is selected from nitrogen and C—$R_{212}$;

$R_{211}$ and $R_{212}$ are independently selected from halogen, hydrogen, CN and $NO_2$;

$R_{213}$ is selected from halogen, haloalkyl, haloalkoxy, —S(O)k$CF_3$, and —$SF_5$; and h and k are independently selected from 0, 1, and 2;

and veterinarily acceptable salts thereof.

By the term "veterinarily acceptable salts" is meant salts the anions of which are known and accepted in the art for the formation of salts for veterinary use. Suitable acid addition salts, e.g. formed by compounds of formulae (I) and (XX) containing a basic nitrogen atom, e.g. an amino group, include salts with inorganic acids, for example hydrochlorides, sulphates, phosphates and nitrates and salts with organic acids for example acetic acid.

Unless otherwise specified, alkyl and alkoxy groups are generally lower alkyl and alkoxy groups, that is having from one to six carbon atoms, preferably from one to four carbon atoms. Generally, the haloalkyl, haloalkoxy and alkylamino groups have from one to four carbon atoms. The haloalkyl and haloalkoxy groups can bear one or more halogen atoms; preferred groups of this type include —$CF_3$ and —$OCF_3$. Cycloalkyl groups generally have from 3 to 6 carbon atoms, preferably from 3 to 5 carbon atoms and may be substituted by one or more halogen atoms. Alkenyl, haloalkenyl, alkynyl, and haloalkynyl groups generally contain from 3 to 5 carbon atoms. By the term aryl is generally meant phenyl, pyridyl, furyl, and thiopheneyl, each of which is optionally substituted by one or more halogen, alkyl, haloalkyl, nitro, alkoxy, haloalkoxy, hydroxy, amino, alkylamino or dialkylamino. In compounds of formula (I), by the term substituted alkyl is meant alkyl which is substituted by one or more halogen, alkoxy, haloalkoxy, amino, alkylamino, dialkylamino, cyano or —S(O)$_m R_{15}$; or alkyl substituted by phenyl or pyridyl each of which is optionally substituted with one or more groups selected from halogen, nitro and alkyl; wherein $R_{15}$ is alkyl or haloalkyl and m is zero, one or two. Preferably in compounds of formula (I), alkyl groups are generally substituted by from one to five halogen atoms, preferably from one to three halogen atoms. Chlorine and fluorine atoms are preferred.

Compounds of formula (I) wherein $R_4$ is —N=C($R_5$)-Z-$R_6$, Z is $NR_7$ and $R_6$ represents a hydrogen atom may exist as the tautomeric double bond isomer form —NH—C($R_5$)=N—$R_7$. It is to be understood that both such forms are embraced by the present invention.

In compounds of formula (XX) the following examples of radicals are provided:

An example of cycloalkylalkyl is cyclopropylmethyl;
an example of cycloalkoxy is cyclopropyloxy;
an example of alkoxyalkyl is $CH_3OCH_2$—;
an example of alkoxyalkoxy is $CH_3OCH_2O$—;
An example of alkoxyalkoxyalkoxy is $CH_3OCH_2OCH_2O$—;
An example of aryloxy is the phenoxy radical; and
An example of the arylalkoxy radical is benzyloxy or 2-phenylethoxy.

Generally, in dialkylamino or di(haloalkyl)amino radicals, the alkyl and haloalkyl groups on nitrogen may be chosen independently of one another.

It is also to be understood that enantiomeric and diastereomeric forms of the compounds of formulae (I) and (XX) and salts thereof are embraced by the present invention. Compounds of formula (I) may be generally prepared according to known processes, for example as described in European Patent Application 511845 or other processes according to the knowledge of a man skilled in the art of chemical synthesis.

A preferred class of compounds of formula (I) for use in the control of parasites in animals are those wherein:

$R_1$ is cyano or alkyl;
$R_2$ is S(O)$_n R_3$;
$R_3$ is alkyl or haloalkyl;
$R_4$ is —N=C($R_5$)-Z-$R_6$;
$R_5$ is hydrogen, alkyl or haloalkyl;
Z is O, S(O)$_a$; or $NR_7$;
$R_6$ and $R_7$ are independently selected from hydrogen and unsubstituted or substituted alkyl; or
$R_6$ and $R_7$ may form together with the nitrogen to which they are attached a 3 to 7 membered ring which may additionally contain one or more heteroatoms selected from oxygen, nitrogen or sulfur; X is selected from nitrogen and C—$R_{12}$;
$R_{11}$ and $R_{12}$ are independently selected from halogen, hydrogen, CN and $NO_2$;
$R_{13}$ is selected from halogen, haloalkyl, haloalkoxy, —S(O)$_q CF_3$, and —$SF_5$;
a, n and q are independently selected from 0, 1, and 2.

Preferably $R_6$ is alkyl which is substituted by one or more halogen, alkoxy, haloalkoxy, amino, alkylamino, dialkylamino, sulfide, sulfoxide, sulfone, or phenyl or pyridyl moieties of which each phenyl or pyridyl moiety is optionally substituted with one or more groups selected from halo, nitro, and alkyl.

Preferably the compound useful in the method of the invention has one or more of the following features:

$R_1$ is cyano;
$R_4$ is —N=C($R_5$)-Z-$R_6$ and Z is —$NR_7$;
X is C—$R_{12}$; $R_{11}$ and $R_{12}$ represent a chlorine atom; and $R_{13}$ is $CF_3$, $OCF_3$ or —$SF_5$;
$R_{12}$ is —S(O)$_n CF_3$ and n is 0, 1, or 2.

A further preferred class of compounds of formula (I) for use in the method of the present invention are those wherein:

$R_1$ is cyano or alkyl; $R_4$ is —N=C($R_5$)-Z-$R_6$; and $R_5$ is hydrogen or $C_1$–$C_3$ alkyl.

The compounds of formula (I), preferably have one or more of the following features:

$R_1$ is cyano or methyl;
$R_3$ is halomethyl (preferably CF3);
$R_{11}$ and $R_{12}$ each independently represent a halogen atom;
X is C—$R_{12}$;
$R_{13}$ is haloalkyl (preferably $CF_3$), haloalkoxy (preferably $OCF_3$), or —$SF_5$; or
n is 0, 1 or 2 (preferably 0 or 1).

A further preferred class of compounds of formula (I) for use in the control of parasites in animals are those wherein:

$R_1$ is cyano;
$R_2$ is S(O)n$R_3$;
$R_3$ is halomethyl;
$R_4$ is —N=C($R_5$)-Z-$R_6$;
Z is $NR_7$;
$R_5$ is hydrogen or alkyl;
$R_6$ and $R_7$ each independently represent hydrogen, alkyl, alkenyl or alkynyl; or alkyl substituted by one or more halogen, alkoxy, haloalkoxy, amino, alkylamino, dialkylamino, cyano or —S(O)m$R_{15}$; or alkyl substituted by phenyl or pyridyl which rings are optionally substituted with one or more groups selected from halogen, nitro and alkyl;

X is selected from nitrogen and C—$R_{12}$;

$R_{11}$ and $R_{12}$ each independently represent a halogen atom;

$R_{13}$ is selected from haloalkyl, haloalkoxy and —SF$_5$;

$R_{15}$ is alkyl or haloalkyl; and m and n are independently selected from 0, 1, and 2.

A further preferred class of compounds of formula (I) is that wherein:

$R_1$ is cyano;

$R_2$ is S(O)$_n$CF$_3$;

$R_4$ is —N=C($R_5$)-Z-$R_6$ or —N=C($R_5$)—N($R_7$)—$R_8$;

Z is N$R_7$;

$R_5$ is hydrogen or alkyl;

$R_6$ and $R_7$ each independently represent hydrogen, alkyl, alkenyl or alkynyl; or alkyl substituted by one or more halogen, alkoxy, haloalkoxy, amino, alkylamino, dialkylamino, cyano or —S(O)$_m$$R_{15}$; or methyl substituted by phenyl or pyridyl which rings are optionally substituted with one or more groups selected from halogen, nitro and alkyl;

$R_8$ is alkoxy, haloalkoxy, amino, alkylamino, dialkylamino or —S(O)$_t$$R_{10}$;

X is selected from nitrogen and C—$R_{12}$;

$R_{10}$ and $R_{15}$ independently represent alkyl or haloalkyl;

$R_{11}$ and $R_{12}$ each represent a chlorine atom;

$R_{13}$ is CF$_3$ or —SF$_5$; and m and n are 0, 1 or 2; and t is 0 or 2.

A further preferred class of compounds of formula (I) are those wherein:

$R_1$ is cyano;

$R_2$ is S(O)$_n$CF$_3$;

$R_4$ is —N=C($R_5$)-Z-$R_6$;

Z is N$R_7$;

$R_5$ is hydrogen or methyl;

$R_6$ and $R_7$ each independently represent hydrogen, alkyl, alkenyl or alkynyl; or alkyl substituted by one or more halogen, alkoxy, haloalkoxy, amino, alkylamino, dialkylamino, cyano or —S(O)$_m$$R_{15}$; or alkyl substituted by phenyl or pyridyl which rings are optionally substituted with one or more groups selected from halogen, nitro and alkyl;

X is C—$R_{12}$;

$R_{11}$ and $R_{12}$ each represent a chlorine atom;

$R_{13}$ is CF$_3$ or —SF$_5$;

$R_{15}$ is alkyl or haloalkyl;

m is zero, one or two; and n is 0 or 1.

A further preferred class of compounds of formula (I) are those wherein:

$R_1$ is cyano;

$R_2$ is S(O)$_n$CF$_3$;

$R_4$ is —N=C($R_5$)-Z-$R_6$;

Z is N$R_7$;

$R_5$ and $R_7$ each represent a hydrogen atom;

$R_6$ is alkyl or haloalkyl;

X is C—$R_{12}$;

$R_{11}$ and $R_{12}$ each represent a chlorine atom;

$R_{13}$ is CF$_3$ or —SF$_5$; and n is 0.

Compounds of formula (XX) which are preferred according to the present invention are those wherein:

$R_{201}$ is cyano;

$R_{202}$ is S(O)$_h$$R_{203}$;

$R_{203}$ is alkyl or haloalkyl;

$R_{204}$ is —N($R_{205}$)C(O)C$R_{206}$$R_{207}$$R_{208}$;

$R_{205}$ is alkyl, haloalkyl, cycloalkyl, cycloalkylalkyl and halocycloalkylalkyl;

$R_{206}$ is alkoxy, haloalkoxy, or hydrogen;

$R_{207}$ and $R_{208}$ are independently hydrogen, alkyl, or haloalkyl; or $R_{207}$ and $R_{208}$ may form together with the carbon to which they are attached a 3 to 7 membered ring which additionally may contain one or more heteroatoms selected from nitrogen, oxygen and sulfur;

$X_1$ is selected from nitrogen and C—$R_{212}$;

$R_{211}$ and $R_{212}$ are independently selected from halogen, hydrogen, CN and NO$_2$;

$R_{213}$ is selected from halogen, haloalkyl, haloalkoxy, —S(O)$_k$CF$_3$, and —SF5; and h and k are independently selected from 0, 1, and 2.

A preferred group of compounds of formula (XX) is that wherein the ring which is formed by $R_{207}$ and $R_{208}$ is interrupted by one or more heteroatoms, more preferably one oxygen atom.

The compounds of formula (XX) of the present invention preferably have one or more of the following features:

$R_{201}$ is cyano;

$R_{203}$ is halomethyl, preferably CF3;

$R_{211}$ and $R_{212}$ are independently halogen;

$X_1$ is C—$R_{212}$;

$R_{213}$ is haloalkyl, haloalkoxy or —SF$_5$; or h is 0 or 1, or 2, preferably 0 or 1.

A preferred class of compounds that wherein $R_{204}$ is N($R_{205}$)C(O)C$R_{206}$$R_{207}$$R_{208}$.

Another preferred class of compounds that wherein $R_{204}$ is N($R_{205}$)C(O)aryl.

Another preferred class of compounds that wherein $R_{204}$ is N($R_{205}$)C(O)O$R_{207}$.

Preferably $R_{205}$ is $C_1$–$C_4$ alkyl, more preferably $C_1$–$C_2$ alkyl, most preferably methyl.

Preferably $R_{206}$ is alkoxy, most preferably methoxy, ethoxy or propoxy.

Preferably $R_{207}$ and $R_{208}$ are both hydrogen.

In another aspect of the present invention, compounds of formula (XX) wherein R204 is —N(R205)C(O) CR206R207R208, N(R205)C(O)aryl, or N(R205)C(O) OR207 are generally prepared from compounds of formula (XXI):

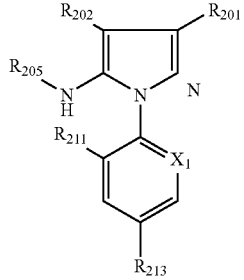

(XXI)

respectively by reaction with halides of formulae X2C(O) CR206R207R208, X2C(O)aryl, or X2C(O)OR207, wherein R201, R202, R205, R206, R207, R208, R211, R213, and X1 are defined above and wherein X2 is a halogen atom. The reaction is generally carried out in the presence of a base, generally using from 1 to 10 molar equivalents of the halide, and is preferably conducted in the presence of an organic solvent such as tetrahydrofuran, methylene chloride, at a temperature of from 0° C. to 150° C. Compounds of formula (XXI) may be prepared from a compound of formula (XXII):

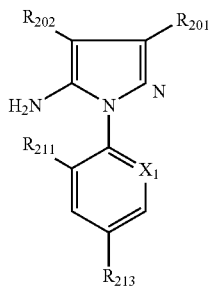

(XXII)

by reaction with a compound of formula (XXIII):

X2R205 (XXIII)

wherein R201, R202, R205, R211, R213, X1 and X2 are defined above. Compounds of formula (XXIII) are generally known in the art as alkylhalides or substituted alkylhalides. Compounds of formula XXII may be prepared by methods described in International Patent Publications WO 87/3781, WO 93/6089, WO 94/21606, WO 97/07102, WO 98/24767, WO 98/28277, WO 98/28278 and WO 98/28279, European Patent Application 295117, 659745, 846686, and U.S. Pat. No. 5,232,940 or other methods known to the person skilled in the art.

Alternatively compounds of formula (XXI) may be prepared by reduction of compounds of formula (XXV):

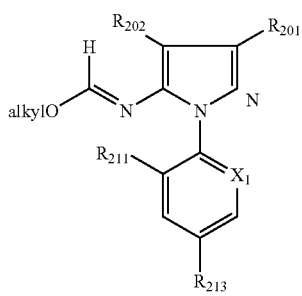

(XXIV)

wherein R201, R202, R211, R213 and X1 are defined above. The reduction generally is effected by the use of a standard hydride ion donor, for example sodium borohydride or sodium cyanoborohydride. The reaction is generally effected in an polar solvent such as ethanol or methanol and generally using from 1 to 10 molar equivalents of the hydride, and is preferably conducted at temperature of from −100° C. to 150° C.

Compounds of formula (XXIV) may be prepared using methods described in EP 295117, WO 97/22593 or other methods known to those skilled in the art.

A particularly preferred compound for use in the method of the present invention is 3-cyano-1-(2,6-dichloro-4-trifluoromethyl)phenyl-5-N-(ethoxyacetyl)-N-methyl-4 trifluoromethylsulfinyl-pyrazole.

Most preferably, the following compounds of formula (I) and (XX) are preferred according to the present invention as listed in Tables 1 to 13. The Compound Numbers are for identification purposes only. The following symbols are hereby defined: Me means methyl; Et means ethyl; n-Pr means n-propyl; i-Pr means isopropyl; n-Bu means n-Butyl, and n-Pent means n-Pentyl; Cy means cyclopropyl.

TABLE 1

Compounds of formula (I) wherein $R_1$ is cyano; $R_2$ is $SCF_3$; $R_{11}$ is Cl, X is C—Cl, $R_4$ is —N=C($R_5$)$ZR_6$, Z is $NR_7$, $R_7$ is H, and $R_{13}$ is $CF_3$ or $SF_5$.

| Compound Number ($R_{13}$ = $CF_3$) | Compound Number ($R_{13}$ = $SF_5$) | $R_5$ | $R_6$ |
|---|---|---|---|
| 201-1 | 201-2 | Me | Me |
| 202-1 | 202-2 | Me | Et |
| 203-1 | 203-2 | Me | n-Pr |
| 204-1 | 204-2 | Me | i-Pr |
| 205-1 | 205-2 | Me | n-Bu |
| 206-1 | 206-2 | H | H |
| 207-1 | 207-2 | H | Et |
| 208-1 | 208-2 | H | n-Pr |
| 209-1 | 209-2 | H | i-Pr |
| 210-1 | 210-2 | H | n-Bu |
| 211-1 | 211-2 | H | $CH_2CF_3$ |
| 212-1 | 212-2 | H | $(CH_2)_2CF_3$ |
| 213-1 | 213-2 | H | $CH_2OMe$ |
| 214-1 | 214-2 | H | $(CH_2)_2OCF_3$ |
| 215-1 | 215-2 | Me | $CH_2CF_3$ |
| 216-1 | 216-2 | Me | $(CH_2)_2CF_3$ |
| 217-1 | 217-2 | Me | $(CH_2)_2OMe$ |
| 218-1 | 218-2 | Me | $(CH_2)_2NMe_2$ |

TABLE 2

Compounds of formula (I) wherein $R_1$ is cyano; $R_{11}$ is Cl; $R_4$ is —N=C($R_5$)$ZR_6$ and Z is $NR_7$.

| Cmpd No. | $R_2$ | $R_5$ | $R_6$ | $R_7$ | X | $R_{13}$ |
|---|---|---|---|---|---|---|
| 219 | $SCF_3$ | H | $CH_3$ | $CH_3$ | C—Cl | $CF_3$ |
| 220 | $SO_2CF_3$ | H | $CH_3$ | $CH_3$ | C—Cl | $CF_3$ |
| 221 | $SCF_3$ | H | $CH_2CN$ | H | C—Cl | $CF_3$ |
| 222 | $SCF_3$ | H | $CH_3$ | H | C—Cl | $CF_3$ |
| 223 | $SOCF_3$ | H | $CH_2Ph$ | H | C—Cl | $CF_3$ |
| 224 | $SCF_3$ | H | $CH_2Ph$ | H | C—Cl | $CF_3$ |
| 225 | $SOCF_3$ | H | $CH_3$ | H | C—Cl | $CF_3$ |
| 226 | $SOCF_3$ | H | $CH_3$ | H | C—Cl | $CF_3$ |
| 227 | $SOCF_3$ | H | $CH_2CF_3$ | H | C—Cl | $CF_3$ |
| 228 | $SO_2CF_3$ | H | 2-propynyl | H | C—Cl | $CF_3$ |
| 229 | $SO_2CF_3$ | H | $CH_2Ph$ | H | C—Cl | $CF_3$ |
| 230 | $SO_2CF_3$ | H | $CH_2CF_3$ | H | C—Cl | $CF_3$ |
| 231 | $SOCF_3$ | H | $CH_3$ | H | C—Cl | $CF_3$ |
| 232 | $SCF_3$ | H | $CH_2CF_3$ | $CH_3$ | C—Cl | $CF_3$ |
| 233 | $SCF_3$ | H | $CH_2CF_3$ | H | C—Cl | $CF_3$ |
| 234 | $SCF_3$ | H | 2-propynyl | H | C—Cl | $CF_3$ |
| 235 | $SCF_3$ | H | 2-propynyl | H | C—Cl | $CF_3$ |
| 236 | $SOCF_3$ | H | 2-propynyl | H | C—Cl | $CF_3$ |
| 237 | $SCF_3$ | H | $CH_2OEt$ | H | N | $CF_3$ |
| 238 | $SCF_3$ | H | $CH_2OCH_2CF_3$ | $CH_3$ | C—Cl | $CF_3$ |
| 239 | $SO_2CF_3$ | H | $CH_2CF_3$ | $CH_3$ | C—Cl | $SF_5$ |
| 240 | $SCF_3$ | H | $CH_2CF_3$ | H | N | $SF_5$ |
| 241 | $SOCF_3$ | H | $CH_2CH_2CF_3$ |  | C—Cl | $CF_3$ |
| 242 | $SO_2CF_3$ | H | $(CH_2)_3CH_3$ |  | C—Cl | $CF_3$ |
| 243 | $SCF_3$ | H | $(CH_2)_2N(CH_3)_2$ |  | C—Cl | $CF_3$ |
| 244 | $SO_2CF_3$ | $CH_3$ | $CH_2$(4-Cl Ph) |  | C—Cl | $CF_3$ |
| 245 | $SCF_3$ | H | $CH_2SO_2CF_3$ |  | C—Cl | $CF_3$ |
| 246 | $SCF_3$ | H | $CH_2$(4-pyridyl) |  | C—Cl | $CF_3$ |
| 247 | $SCF_3$ | H | $CH_2$(3-$NO_2Ph$) |  | C—Cl | $CF_3$ |
| 248 | $SCF_3$ | H | $CH_2CH_2SCH_3$ |  | C—Cl | $CF_3$ |
| 249 | $SOCF_3$ | H | $CH_2CF_3$ | $CH_3$ | C—Cl | $CF_3$ |

Note:
Compound number 232 is the acetate salt, and compound number 233 is the citrate salt.

TABLE 3

Compounds of formula (I) wherein $R_1$ is cyano; $R_{11}$ is Cl; and $R_4$ is —N=C($R_5$)—N($R_7$)—$R_8$.

| Cmpd No. | $R_2$ | $R_5$ | $R_8$ | $R_7$ | X | $R_{13}$ |
|---|---|---|---|---|---|---|
| 250 | $SCF_3$ | H | OEt | H | C—Cl | $CF_3$ |
| 251 | $SCF_3$ | H | $NHCH_3$ | H | C—Cl | $CF_3$ |
| 252 | $SCF_3$ | H | $NHCH_3$ | $CH_3$ | C—Cl | $CF_3$ |
| 253 | $SCF_3$ | H | $OCH_2CF_3$ | H | C—Cl | $CF_3$ |
| 254 | $SCF_3$ | H | $N(CH_3)_2$ | H | N | $SF_5$ |
| 255 | $SCF_3$ | H | $NH_2$ | H | C—Cl | $CF_3$ |
| 256 | $SCF_3$ | H | S-nPr | H | C—Cl | $CF_3$ |
| 257 | $SO_2CF_3$ | Et | S-nPr | H | C—Cl | $SF_5$ |
| 258 | $SCF_3$ | H | $SO_2CH_3$ | H | C—Cl | $CF_3$ |

The following compound of the formula (XX) are preferred according to the present invention as listed Tables 4–12.

TABLE 4

Compounds of formula (XX) wherein $R_{201}$ is cyano; $R_{202}$ is $SCF_3$; $R_{204}$ is $N(R_{205})C(O)CR_{206}R_{207}R_{208}$; $R_{207}$ and $R_{208}$ = H; $R_{211}$ is Cl, $X_1$ is C—Cl, and $R_{213}$ is $CF_3$ or $SF_5$.

| Compound Number ($R_{213} = CF_3$) | Compound Number ($R_{213} = SF_5$) | $R_{205}$ | $R_{206}$ |
|---|---|---|---|
| 1-1 | 1-2 | Me | H |
| 2-1 | 2-2 | Me | OMe |
| 3-1 | 3-2 | Me | OEt |
| 4-1 | 4-2 | Me | O-i-Pr |
| 5-1 | 5-2 | Me | O-n-Bu |
| 6-1 | 6-2 | Et | H |
| 7-1 | 7-2 | Et | OMe |
| 8-1 | 8-2 | Et | OEt |
| 9-1 | 9-2 | Et | O-i-Pr |
| 10-1 | 10-2 | Et | O-n-Bu |
| 11-1 | 11-2 | n-Pr | H |
| 12-1 | 12-2 | n-Pr | OMe |
| 13-1 | 13-2 | n-Pr | OEt |
| 14-1 | 14-2 | n-Pr | O-i-Pr |
| 15-1 | 15-2 | n-Pr | O-n-Bu |
| 16-1 | 16-2 | i-Pr | H |
| 17-1 | 17-2 | i-Pr | OMe |
| 18-1 | 18-2 | i-Pr | OEt |
| 19-1 | 19-2 | i-Pr | O-i-Pr |
| 20-1 | 20-2 | i-Pr | O-n-Bu |
| 21-1 | 21-2 | n-Bu | H |
| 22-1 | 22-2 | n-Bu | OMe |
| 23-1 | 23-2 | n-Bu | OEt |
| 24-1 | 24-2 | n-Bu | O-i-Pr |
| 25-1 | 25-2 | n-Bu | O-n-Bu |
| 26-1 | 26-2 | $CH_2Cy$ | H |
| 27-1 | 27-2 | $CH_2Cy$ | OMe |
| 28-1 | 28-2 | $CH_2Cy$ | OEt |
| 29-1 | 29-2 | $CH_2Cy$ | O-i-Pr |
| 30-1 | 30-2 | $CH_2Cy$ | O-n-Bu |
| 31-1 | 31-2 | $CH_2CCH$ | H |
| 32-1 | 32-2 | $CH_2CCH$ | OMe |
| 33-1 | 33-2 | $CH_2CCH$ | OEt |
| 34-1 | 34-2 | $CH_2CCH$ | O-i-Pr |
| 35-1 | 35-2 | $CH_2CCH$ | O-n-Bu |
| 36-1 | 36-2 | Me | OAc |
| 37-1 | 37-2 | Me | $CH_2OMe$ |
| 38-1 | 38-2 | Me | $CH_2OEt$ |
| 39-1 | 39-2 | Me | O-i-Pr |
| 40-1 | 40-2 | Me | O-n-Bu |
| 41-1 | 41-2 | Me | $OCH_2CF_3$ |

TABLE 5

Compounds of formula (XX) wherein $R_{201}$ is cyano; $R_{202}$ is $S(O)CF_3$; $R_{204}$ is $N(R_{205})C(O)CR_{206}R_{207}R_{208}$; $R_{207}$ and $R_{208}$ = H; $R_{211}$ is Cl, $X_1$ is C—Cl, and $R_{213}$ is $CF_3$ or $SF_5$.

| Compound Number ($R_{213} = CF_3$) | Compound Number ($R_{213} = SF_5$) | $R_{205}$ | $R_{206}$ |
|---|---|---|---|
| 1-3 | 1-4 | Me | H |
| 2-3 | 2-4 | Me | OMe |
| 3-3 | 3-4 | Me | OEt |
| 4-3 | 4-4 | Me | O-i-Pr |
| 5-3 | 5-4 | Me | O-n-Bu |
| 6-3 | 6-4 | Et | H |
| 7-3 | 7-4 | Et | OMe |
| 8-3 | 8-4 | Et | OEt |
| 9-3 | 9-4 | Et | O-i-Pr |
| 10-3 | 10-4 | Et | O-n-Bu |
| 11-3 | 11-4 | n-Pr | H |
| 12-3 | 12-4 | n-Pr | OMe |
| 13-3 | 13-4 | n-Pr | OEt |
| 14-3 | 14-4 | n-Pr | O-i-Pr |
| 15-3 | 15-4 | n-Pr | O-n-Bu |
| 16-3 | 16-4 | i-Pr | H |
| 17-3 | 17-4 | i-Pr | OMe |
| 18-3 | 18-4 | i-Pr | OEt |
| 19-3 | 19-4 | i-Pr | O-i-Pr |
| 20-3 | 20-4 | i-Pr | O-n-Bu |
| 21-3 | 21-4 | n-Bu | H |
| 22-3 | 22-4 | n-Bu | OMe |
| 23-3 | 23-4 | n-Bu | OEt |
| 24-3 | 24-4 | n-Bu | O-i-Pr |
| 25-3 | 25-4 | n-Bu | O-n-Bu |
| 26-3 | 26-4 | $CH_2Cy$ | H |
| 27-3 | 27-4 | $CH_2Cy$ | OMe |
| 28-3 | 28-4 | $CH_2Cy$ | OEt |
| 29-3 | 29-4 | $CH_2Cy$ | O-i-Pr |
| 30-3 | 30-4 | $CH_2Cy$ | O-n-Bu |
| 31-3 | 31-4 | $CH_2CCH$ | H |
| 32-3 | 32-4 | $CH_2CCH$ | OMe |
| 33-3 | 33-4 | $CH_2CCH$ | OEt |
| 34-3 | 34-4 | $CH_2CCH$ | O-i-Pr |
| 35-3 | 35-4 | $CH_2CCH$ | O-n-Bu |
| 36-3 | 36-4 | Me | OAc |
| 37-3 | 37-4 | Me | $CH_2OMe$ |
| 38-3 | 38-4 | Me | $CH_2OEt$ |
| 39-3 | 39-4 | Me | O-i-Pr |
| 40-3 | 40-4 | Me | O-n-Bu |
| 41-3 | 41-4 | Me | $OCH_2CF_3$ |

Compound 3-3 was separated into its enantiomers (R)3-3 and (S)3-3.

TABLE 6

Compounds of formula (XX) wherein $R_{201}$ is cyano; $R_{202}$ is $S(O)_2CF_3$; $R_{204}$ is $N(R_{205})C(O)CR_{206}R_{207}R_{208}$; $R_{207}$ and $R_{208}$ = H; $R_{211}$ is Cl, $X_1$ is C—Cl, and $R_{213}$ is $CF_3$ or $SF_5$.

| Compound Number ($R_{213} = CF_3$) | Compound Number ($R_{213} = SF_5$) | $R_{205}$ | $R_{206}$ |
|---|---|---|---|
| 1-5 | 1-6 | Me | H |
| 2-5 | 2-6 | Me | OMe |
| 3-5 | 3-6 | Me | OEt |
| 4-5 | 4-6 | Me | O-i-Pr |
| 5-5 | 5-6 | Me | O-n-Bu |
| 6-5 | 6-6 | Et | H |
| 7-5 | 7-6 | Et | OMe |
| 8-5 | 8-6 | Et | OEt |
| 9-5 | 9-6 | Et | O-i-Pr |
| 10-5 | 10-6 | Et | O-n-Bu |
| 11-5 | 11-6 | n-Pr | H |
| 12-5 | 12-6 | n-Pr | OMe |
| 13-5 | 13-6 | n-Pr | OEt |

TABLE 6-continued

Compounds of formula (XX) wherein $R_{201}$ is cyano; $R_{202}$ is $S(O)_2CF_3$; $R_{204}$ is $N(R_{205})C(O)CR_{206}R_{207}R_{208}$; $R_{207}$ and $R_{208}$ = H; $R_{211}$ is Cl, $X_1$ is C—Cl, and $R_{213}$ is $CF_3$ or $SF_5$.

| Compound Number ($R_{213}$ = $CF_3$) | Compound Number ($R_{213}$ = $SF_5$) | $R_{205}$ | $R_{206}$ |
|---|---|---|---|
| 14-5 | 14-6 | n-Pr | O-i-Pr |
| 15-5 | 15-6 | n-Pr | O-n-Bu |
| 16-5 | 16-6 | i-Pr | H |
| 17-5 | 17-6 | i-Pr | OMe |
| 18-5 | 18-6 | i-Pr | OEt |
| 19-5 | 19-6 | i-Pr | O-i-Pr |
| 20-5 | 20-6 | i-Pr | O-n-Bu |
| 21-5 | 21-6 | n-Bu | H |
| 22-5 | 22-6 | n-Bu | OMe |
| 23-5 | 23-6 | n-Bu | OEt |
| 24-5 | 24-6 | n-Bu | O-i-Pr |
| 25-5 | 25-6 | n-Bu | O-n-Bu |
| 26-5 | 26-6 | $CH_2Cy$ | H |
| 27-5 | 27-6 | $CH_2Cy$ | OMe |
| 28-5 | 28-6 | $CH_2Cy$ | OEt |
| 29-5 | 29-6 | $CH_2Cy$ | O-i-Pr |
| 30-5 | 30-6 | $CH_2Cy$ | O-n-Bu |
| 31-5 | 31-6 | $CH_2CCH$ | H |
| 32-5 | 32-6 | $CH_2CCH$ | OMe |
| 33-5 | 33-6 | $CH_2CCH$ | OEt |
| 34-5 | 34-6 | $CH_2CCH$ | O-i-Pr |
| 35-5 | 35-6 | $CH_2CCH$ | O-n-Bu |
| 36-5 | 36-6 | Me | OAc |
| 37-5 | 37-6 | Me | $CH_2OMe$ |
| 38-5 | 38-6 | Me | $CH_2OEt$ |
| 39-5 | 39-6 | Me | O-i-Pr |
| 40-5 | 40-6 | Me | O-n-Bu |
| 41-5 | 41-6 | Me | $OCH_2CF_3$ |

TABLE 7

Compounds of formula (XX) wherein $R_{201}$ is cyano; $R_{202}$ is $SCF_3$; $R_{204}$ is $N(R_{205})C(O)CR_{206}R_{207}R_{208}$; $R_{211}$ is Cl, $X_1$ is C—Cl, and $R_{213}$ is $CF_3$ or $SF_5$.

| Compound Number ($R_{213}$ = $CF_3$) | Compound Number ($R_{213}$ = $SF_5$) | $R_{205}$ | $R_{206}$ | $R_{207}, R_{208}$ |
|---|---|---|---|---|
| 1-7 | 1-8 | Me | H | —$CH_2CH_2CH_2O$— |
| 2-7 | 2-8 | Et | H | —$CH_2CH_2CH_2O$— |
| 3-7 | 3-8 | i-Pr | H | —$CH_2CH_2CH_2O$— |
| 4-7 | 4-8 | Pr | H | —$CH_2CH_2CH_2O$— |
| 5-7 | 5-8 | Bu | H | —$CH_2CH_2CH_2O$— |
| 6-7 | 6-8 | Cy | H | —$CH_2CH_2CH_2O$— |
| 7-7 | 7-8 | $CH_2Cy$ | H | —$CH_2CH_2CH_2O$— |

Compound 1-7 was also separated into its enantiomers, called (R)1-7 and (S)1-7.

TABLE 8

Compounds of formula (XX) wherein $R_{201}$ is cyano; $R_{202}$ is $S(O)CF_3$; $R_{204}$ is $N(R_{205})C(O)CR_{206}R_{207}R_{208}$; $R_{211}$ is Cl, $X_1$ is C—Cl, and $R_{213}$ is $CF_3$ or $SF_5$.

| Compound Number ($R_{213}$ = $CF_3$) | Compound Number ($R_{213}$ = $SF_5$) | $R_{205}$ | $R_{206}$ | $R_{207}, R_{208}$ |
|---|---|---|---|---|
| 1-9 | 1-10 | Me | H | —$CH_2CH_2CH_2O$— |
| 2-9 | 2-10 | Et | H | —$CH_2CH_2CH_2O$— |
| 3-9 | 3-10 | i-Pr | H | —$CH_2CH_2CH_2O$— |
| 4-9 | 4-10 | Pr | H | —$CH_2CH_2CH_2O$— |
| 5-9 | 5-10 | Bu | H | —$CH_2CH_2CH_2O$— |
| 6-9 | 6-10 | $CH_2Cy$ | H | —$CH_2CH_2CH_2O$— |
| 7-9 | 7-10 | Cy | H | —$CH_2CH_2CH_2O$— |

Compound 1-9 was separated into its diastereomers, (R,R)1-9, (S,R)1-9, (S,S)1-9, and (R,S)1-9. The first designation of absolute configuration refers to the configuration of the sulfoxide moiety, the second to the chiral carbon.

TABLE 9

Compounds of formula (XX) wherein $R_{201}$ is cyano; $R_{202}$ is $S(O)_2CF_3$; $R_{204}$ is $N(R_{205})C(O)CR_{206}R_{207}R_{208}$; $R_{211}$ is Cl, $X_1$ is C—Cl, and $R_{213}$ is $CF_3$ or $SF_5$.

| Compound Number ($R_{213}$ = $CF_3$) | Compound Number ($R_{213}$ = $SF_5$) | $R_{205}$ | $R_{206}$ | $R_{207}, R_{208}$ |
|---|---|---|---|---|
| 1-11 | 1-12A | Me | H | —$CH_2CH_2CH_2O$— |
| 2-11 | 2-12A | Et | H | —$CH_2CH_2CH_2O$— |
| 3-11 | 3-12A | i-Pr | H | —$CH_2CH_2CH_2O$— |
| 4-11 | 4-12A | Pr | H | —$CH_2CH_2CH_2O$— |
| 5-11 | 5-12A | Bu | H | —$CH_2CH_2CH_2O$— |
| 6-11 | 6-12A | Cy | H | —$CH_2CH_2CH_2O$— |
| 7-11 | 7-12A | $CH_2Cy$ | H | —$CH_2CH_2CH_2O$— |

Compound 1-11 was separated into its diastereomers, (R)1-11 and (S)1-11.

TABLE 10

Compounds of formula (XX) wherein $R_{201}$ is cyano; $R_{204}$ is $N(R_{205})C(O)CR_{206}R_{207}R_{208}$; $R_{207}$ and $R_{208}$ are H; $R_{211}$ is Cl, $X_1$ is C—Cl, and $R_{213}$ is $CF_3$ or $SF_5$.

| Compound Number ($R_{213}$ = $CF_3$) | Compound Number ($R_{213}$ = $SF_5$) | $R_{205}$ | $R_{206}$ |
|---|---|---|---|
| $R_{202}$ = $SCF_3$ | | | |
| 1-12 | 1-13 | Cy | H |
| 2-12 | 2-13 | Cy | OMe |
| 3-12 | 3-13 | Cy | OEt |
| 4-12 | 4-13 | Cy | O-i-Pr |
| 5-12 | 5-13 | Cy | O-n-Bu |
| $R_{202}$ = $S(O)CF_3$ | | | |
| 6-12 | 6-13 | Cy | H |
| 7-12 | 7-13 | Cy | OMe |
| 8-12 | 8-13 | Cy | OEt |
| 9-12 | 9-13 | Cy | O-i-Pr |
| 10-12 | 10-13 | Cy | O-n-Bu |
| $R_{202}$ = $S(O)_2CF_3$ | | | |
| 11-12 | 11-13 | n-Pr | H |
| 12-12 | 12-13 | n-Pr | OMe |
| 13-12 | 13-13 | n-Pr | OEt |
| 14-12 | 14-13 | n-Pr | O-i-Pr |
| 15-12 | 15-13 | n-Pr | O-n-Bu |

TABLE 11

Compounds of formula (XX) wherein $R_{201}$ is cyano; $R_{204}$ is $N(R_{205})C(O)CR_{207}$; $R_{211}$ is Cl, $X_1$ is C—Cl, and $R_{213}$ is $CF_3$ or $SF_5$.

| Compound Number ($R_{213}$ = $CF_3$) | Compound Number ($R_{213}$ = $SF_5$) | $R_{205}$ | $R_{207}$ |
|---|---|---|---|
| \multicolumn{4}{c}{$R_{202}$ is $SCF_3$} ||||
| 67-1 | 67-2 | Me | Me |
| 68-1 | 68-2 | Me | Et |
| 69-1 | 69-2 | Me | i-Pr |
| 70-1 | 70-2 | Me | n-Pr |
| 71-1 | 71-2 | Et | Me |
| 72-1 | 72-2 | Et | Et |
| 73-1 | 73-2 | Et | i-Pr |
| 74-1 | 74-2 | Et | n-Pr |
| 75-1 | 75-2 | n-Pr | Me |
| 76-1 | 76-2 | n-Pr | Et |
| 77-1 | 77-2 | n-Pr | i = Pr |
| 78-1 | 78-2 | n-Pr | n-Pr |
| 79-1 | 79-2 | i-Pr | Me |
| 80-1 | 80-2 | i-Pr | Et |
| 81-1 | 81-2 | i-Pr | i-Pr |
| 82-1 | 82-2 | i-Pr | n-Pr |
| \multicolumn{4}{c}{$R_{202}$ is $S(O)CF_3$} ||||
| 83-1 | 83-2 | Me | Me |
| 84-1 | 84-2 | Me | Et |
| 85-1 | 85-2 | Me | i-Pr |
| 86-1 | 86-2 | Me | n-Pr |
| 87-1 | 87-2 | Et | Me |
| 88-1 | 88-2 | Et | Et |
| 89-1 | 89-2 | Et | i-Pr |
| 90-1 | 90-2 | Et | n-Pr |
| 91-1 | 91-2 | n = Pr | Me |
| 92-1 | 92-2 | n-Pr | Et |
| 93-1 | 93-2 | n-Pr | i-Pr |
| 94-1 | 94-2 | n-Pr | n-Pr |
| 95-1 | 95-2 | i-Pr | Me |
| 96-1 | 96-2 | i-Pr | Et |
| 97-1 | 97-2 | i-Pr | i-Pr |
| 98-1 | 98-2 | i-Pr | n-Pr |
| \multicolumn{4}{c}{$R_{202}$ is $S(O)_2CF_3$} ||||
| 99-1 | 99-2 | Me | Me |
| 100-1 | 100-2 | Me | Et |
| 101-1 | 101-2 | Me | i-Pr |
| 102-1 | 102-2 | Me | n-Pr |
| 103-1 | 103-2 | Et | Me |
| 104-1 | 104-2 | Et | Et |
| 105-1 | 105-2 | Et | i-Pr |
| 106-1 | 106-2 | Et | n-Pr |
| 107-1 | 107-2 | n-Pr | Me |
| 108-1 | 108-2 | n-Pr | Et |
| 109-1 | 109-2 | n-Pr | i-Pr |
| 110-1 | 110-2 | n-Pr | n-Pr |
| 111-1 | 111-2 | i-Pr | Me |
| 112-1 | 112-2 | i-Pr | Et |
| 113-1 | 113-2 | i-Pr | i-Pr |
| 114-1 | 114-2 | i-Pr | n-Pr |

TABLE 12

Compounds of formula (XX) wherein $R_{201}$ is cyano; $R_{202}$ is $S(O)_hCF_3$; $R_{204}$ is $N(R_{205})C(O)CR_{206}R_{207}R_{208}$; $R_{211}$ is Cl, $X_1$ is C—Cl, and $R_{213}$ is $CF_3$ or $SF_5$.

| Compound Number ($R_{213}$ = $CF_3$) | Compound Number ($R_{213}$ = $SF_5$) | h | $R_{205}$ | $R_{206}$ | $R_{207}$ | $R_{208}$ |
|---|---|---|---|---|---|---|
| 115-1 | 115-2 | 0 | Me | H | Me | Me |
| 116-1 | 116-2 | 0 | Me | OEt | H | Me |
| 117-1 | 117-2 | 0 | Me | H | cyclopropyl ||
| 118-1 | 118-2 | 0 | Me | OMe | H | Me |
| 119-1 | 119-2 | 0 | Me | OEt | Me | Me |
| 120-1 | 120-2 | 2 | Me | OCH$_2$CH$_2$OMe | H | H |
| 121-1 | 121-2 | 0 | Me | H | —CH$_2$CH$_2$CH$_2$CH$_2$O— ||
| 122-1 | 122-2 | 1 | Me | OEt | H | Me |
| 123-1 | 123-2 | 0 | Me | H | H | Me |
| 124-1 | 124-2 | 0 | Me | H | H | Et |

TABLE 13

Compounds of formula (XX) wherein $R_{201}$ is cyano; $R_{202}$ is $S(O)_hCF_3$; $R_{204}$ is $N(R_{205})C(O)$aryl; $R_{211}$ is Cl, $X_1$ is C—Cl, $R_{205}$ is $CH_3$; and $R_{213}$ is $CF_3$ or $SF_5$.
Within this table the following symbols are defined:
Ph means phenyl; Fu means furyl
Th means the thiophene radical
Pyr means pyridyl

| Compound Number ($R_{213} = CF_3$) | Compound Number ($R_{213} = SF_5$) | aryl |
|---|---|---|
| $R_{202}$ is $SCF_3$ | | |
| 125-1 | 125-2 | Ph |
| 126-1 | 126-2 | 4-OMe-Ph |
| 127-1 | 127-2 | 4-CF$_3$-Ph |
| 128-1 | 128-2 | 2-Th |
| 129-1 | 129-2 | 3-Th |
| 130-1 | 130-2 | 2-Fu |
| 131-1 | 131-2 | 3-Fu |
| 132-1 | 132-2 | 2-Pyr |
| 133-1 | 133-2 | 3-Pyr |
| 134-1 | 134-2 | 4-Pyr |
| 135-1 | 135-2 | 6-Cl-2-Pyr |
| 136-1 | 136-2 | 6-CF$_3$-2-Pyr |
| 137-1 | 137-2 | 5-Cl-2-Fu |
| 138-1 | 138-2 | 5-CF$_3$-2-Fu |
| 139-1 | 139-2 | 5-OMe-2-Th |
| 140-1 | 140-2 | 5-CF$_3$-2-Th |
| $R_{202}$ is $S(O)CF_3$ | | |
| 125-3 | 125-4 | Ph |
| 126-3 | 126-4 | 4-OMe-Ph |
| 127-3 | 127-4 | 4-CF$_3$-Ph |
| 128-3 | 128-4 | 2-Th |
| 129-3 | 129-4 | 3-Th |
| 130-3 | 130-4 | 2-Fu |
| 131-3 | 131-4 | 3-Fu |
| 132-3 | 132-4 | 2-Pyr |
| 133-3 | 133-4 | 3-Pyr |
| 134-3 | 134-4 | 4-Pyr |
| 135-3 | 135-4 | 6-Cl-2-Pyr |
| 136-3 | 136-4 | 6-CF$_3$-2-Pyr |
| 137-3 | 137-4 | 5-Cl-2-Fu |
| 138-3 | 138-4 | 5-CF$_3$-2-Fu |
| 139-3 | 139-4 | 5-OMe-2-Th |
| 140-3 | 140-4 | 5-CF$_3$-2-Th |
| $R_{202}$ is $S(O)_2CF_3$ | | |
| 125-5 | 125-6 | Ph |
| 126-5 | 126-6 | 4-OMe-Ph |
| 127-5 | 127-6 | 4-CF$_3$-Ph |
| 128-5 | 128-6 | 2-Th |
| 129-5 | 129-6 | 3-Th |
| 130-6 | 130-6 | 2-Fu |
| 131-5 | 131-6 | 3-Fu |
| 132-5 | 132-6 | 2-Pyr |
| 133-5 | 133-6 | 3-Pyr |
| 134-5 | 134-6 | 4-Pyr |
| 135-5 | 135-6 | 6-Cl-2-Pyr |
| 136-5 | 136-6 | 6-CF$_3$-2-Pyr |
| 137-5 | 137-6 | 5-Cl-2-Fu |
| 138-5 | 138-6 | 5-CF$_3$-2-Fu |
| 139-5 | 139-6 | 5-OMe-2-Th |
| 140-5 | 140-6 | 5-CF$_3$-2-Th |

The composition comprising the ectoparasiticide may further comprise inactive ingredients such as carriers, diluents, solvents, cosolvents and crystallization inhibitors. The ectoparasiticide is present in an amount effective to reduce larvae, nymphs or ticks on a small rodent upon topical application. Preferably, the ectoparasiticide, especially the compound of formula (I) or (XX), is present in the composition at a concentration of from 0.1% to 5%, and preferably from 0.25% to 1%, and most preferably from 0.4% to 0.9% (weight/weight).

The composition is preferably substantially hydrophobic. Further, the composition is long-lasting such that it can be transferred to rodents with maintenance of ectoparasiticidal activity for up to three months, preferably six to eight months after placement at the locus, and more preferably for up to ten months, and most preferably for up to twelve months after placement at the locus.

In a preferred embodiment, the composition comprises a compound of formula (I) or (XX), a crystallization inhibitor, an organic solvent, and an organic cosolvent. The composition is preferably hydrophobic. The crystallization inhibitor is preferably present at a concentration of 1 to 20% (w/v), and more preferably 5 to 15% (w/v).

A crystallization inhibitor prevents crystallization of the compound of formula (I) or (XX) from the composition on the applicator or the hair or skin of the rodent. A crystallization inhibitor is defined by a test in which 0.3 ml of a solution containing 10% (w/v) of a compound of formula (I) or (XX) in a solvent as defined hereinbelow and 10% of the putative inhibitor is placed on a glass slide at 20° C. for 24 hours. The presence of less than 10 crystals, a preferably few or no crystals, by observation with the naked eye after 24 hours is indicative of an inhibitor as defined herein.

Examples of crystallization inhibitors which can be used in the invention include polyvinylpyrrolidone, polyvinyl alcohols, copolymers of vinyl acetate and vinylpyrrolidone, polyethylene glycols, benzyl alcohol, mannitol, glycerol, sorbitol, polyethoxylated sorbitan esters; lecithin, carboxymethylcellulose sodium, acrylic derivatives such as methacrylate and others;

anionic surfactants such as alkali metal stearates, especially of sodium, of potassium or of ammonium; calcium stearate; triethanolamine stearate, sodium abietate; cetylsulphates, especially sodium laurylsulphate and sodium cetylsulphate; sodium dodecylbenzenesulphonate, sodium dioctylsulphosuccinate; fatty acids, especially those derived from copra oil;

cationic surfactants such as water-soluble quaternary ammonium salts of formula N$^+$R'R"R'"R""Y' in which the radicals R', R", R'", and R"" are, independent of one another, optionally hydroxylated hydrocarbon radicals, and Y' is an anion of a strong acid, such as halide, sulphate and sulphonate anions; including in particular cetyltrimethylammonium bromide;

the amine salts of formula N$^+$R'R"R'" in which the radicals R', R", and R'" are, independent of one another, optionally hydroxylated hydrocarbon radicals; including in particular octadecylamine hydrochloride;

non-ionic surfactants such as optionally polyethoxylated sorbitan esters, in particular Polysorbate 80, polyethoxylated alkyl ethers; polyethylene glycol stearate, polyethoxylated castor oil derivatives, polyglycerol esters, polyethoxylated fatty alcohols, polyethoxylated fatty acids, copolymers of ethylene oxide and propylene oxide; and amphoteric surfactants such as substituted lauryl betaine compounds, or preferably a mixture of at least two of these.

Most preferably, a crystallization inhibitor pair will be used, namely the combination of a surface-active agent and a filmogenic agent. Preferred filmogenic agents include different grades of polyvinylpyrrolidone, polyvinyl alcohol, and copolymers of vinyl acetate and vinylpyrrolidone. Preferred surface active agents include non-ionic surfactants, preferably polyethoxylated esters of sorbitan and especially the different grades of polysorbates, for example Polysorbate 80. The filmogenic agent and surface-active agent may be incorporated in close or identical quantities the total of which is within the preferred concentration range for the crystallization inhibitor as described above.

The organic solvent preferably has a dielectric constant of from 10 to 35, preferably from 20 and 30. The content of this organic solvent in the total composition preferably represents the remainder to 100% of the composition.

The organic cosolvent preferably has a boiling point lower than 100° C., preferably lower than 80° C., and a dielectric constant of from 10 to 40, preferably of from 20 to 30. The cosolvent is preferably present in the composition according to a weight/weight (w/w) ratio of co-solvent/solvent of from 1/15 to 1/2. The cosolvent is volatile in order to promote drying and is miscible with water and/or with the solvent. Although not preferred, the composition can optionally comprise water, especially at a rate from 0 to 30% volume/volume (v/v), preferably from 0 to 5%. The composition according to the invention may also comprise an antioxidant agent intended to inhibit oxidation in the air, this agent especially being present at a rate of from 0.005 to 1% (W/V), preferably from 0.01 to 0.05%.

Examples of organic solvents according to the invention include acetone, acetonitrile, benzyl alcohol, butyl diglycol, dimethyl acetamide, dimethyl formamide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone, especially N-methyl-pyrrolidone, diethylene glycol monoethyl ether, ethylene glycol, diethyl phthalate, or a mixture of at least two of these.

Suitable cosolvents for use in the present compositions include alcohols, such as absolute ethanol, isopropanol, and methanol. As antioxidant agent, conventional agents are especially used, such as butylhydroxyanisole, butyl-hydroxytoluene, ascorbic acid, sodium metabisulphite, propyl gallate, sodium thiosulphate, or a mixture of at least two of these.

Oils may advantageously be utilized in the compositions of the invention. For example, heavy oils such as mineral or vegetable including corn, soybean and peanut oil, and petroleum fractions such as paraffinic or aromatic hydrocarbons may be used.

The compositions according to the invention are generally prepared by simple mixing of the constituents as defined above.

The method of the invention provides to the rodent a dose of ectoparasiticide which is substantially harmless to the rodent. Preferably the amount of active ingredient applied to the rodent is from 0.001 mg to about 1 mg per application within the bait, preferably from 0.01 mg to 0.05 mg. The method of the invention also provides a small dose per application such that if an individual rodent visits the locus multiple times, the rodent is not harmed.

Such a dose must be able to protect the rodent itself for a period of at least one month, preferably from 1 to 3 months, and more preferably from 1 to 9 months. It is also provided according to the present invention that the rodents are not repelled from the enclosure so that they may be redosed by re-entering the enclosure. There may be an attractant associated with the enclosure which is highly attractive to the rodents in order to quickly dose many rodents within a predetermined area. A foodstuff may be associated with the enclosure. Most preferably, there is no poison for the rodent.

As a matter of an appropriate, safe method of providing such an enclosure to rodents in the loci which they are inhabiting or expected to inhabit, which loci are generally near humans, it is highly preferred that the ectoparasiticide composition in use be substantially inaccessible to the human hand. That is the ordinary user of such an enclosure would not be able to reach in or on the enclosure and be dosed with the ectoparasiticide.

Generally, the enclosure is placed at a transition zone which zone defines an interface between a woodland and a property where humans dwell. The enclosures are spaced one from another from 10 to 50 feet, preferably from 20 to 40 feet. Generally the enclosures are placed at the perimeter of the property. If the property is itself a woodland per se, there may be a grid of enclosures laid out to dose rodents within the property. The interface may be a verge.

Generally, there are from 1 to 50 enclosures placed per hectare within a defined area to be treated, preferably from 2 to 40, and more preferably from 10 to 35 enclosures per hectare.

In a park or other public facility, enclosures may be spaced along trails where humans may pass. Generally in such a setting, enclosures may be placed on one or both sides of a trail.

Preferably the enclosures may be placed and replaced on a periodic basis. In such a way, the method of the present invention provides a barrier to arthropods which may carry diseases. Each time the enclosures are replaced or replenished with the ectoparasiticide, the barrier is rejuvenated. The enclosures may be replaced or replenished from once per year to three times per year, depending on the population of rodents in the barrier locus.

In a particularly desirable aspect of the invention, there is provided a method of interrupting a disease cycle caused by arthropods of small rodents which method comprises treating a defined area by providing one or more enclosures of appropriate size to such rodents, the enclosures having one or more peripheral openings allowing entry and egress of rodents, the enclosure including at least one applicator arranged to contact a rodent; providing a composition comprising an ectoparasiticide on the applicator; and placing one or more enclosures in a locus where the rodents are expected, wherein the applicator is arranged and the composition is provided to apply an effective amount of the composition to the skin or hair of the rodent upon contact with the applicator.

In this aspect of the invention there is not a general expunging of the arthropod population away from the defined area, but rather a reduction in the infectious agent in that defined area.

The enclosure generally contains from 0.001 g to 1 g of active ingredient per device preferably from 0.01 g to 1 g of active ingredient, most preferably from 0.05 g to 0.150 g per device.

In general, in a highly preferred embodiment, the amount of compound of formula (I) used per hectare is from 0.1 g/ha to 3 g/ha per 6 months of use. More preferably, the amount of the compound of formula (I) is from 0.2 to 2 g per hectare per 6 months. In this way, the method of according to the invention may substantially reduce the number of rodents with the parasite per predetermined land area.

In a preferred embodiment, the enclosure has at least one peripheral opening to allow entry and egress of rodents and an applicator provided with an ectoparasiticide composition. More preferably, the enclosure further defines a passageway through which a rodent is attracted to proceed. As rodents are generally curious and seek out small spaces in which to lodge themselves or burrow or find food, this is a highly advantageous way in which to dose the rodents.

In the enclosure, the applicator is generally disposed in the path of the rodent, that is in the passageway. The applicator may be a small mop head, brush, wick, adsorbent panel or strip attached to the top of the enclosure or may be an insert lodged in a cavity in an interior wall which defines the passageway. In one preferred embodiment, the applicator is arranged to contact the anterior portion of a rodent that has entered the enclosure. The enclosure may include a bait located therein and the passageway is preferably arranged between the opening and the bait. The applicator may be rechargeable or replaceable, preferably from outside the enclosure and without opening the enclosure. The composition may be applied to the applicator in a manner suitable to the particular applicator, for example, by soaking or dipping the applicator in the composition, or painting, spraying, squirting or otherwise applying the composition to the applicator.

The enclosure preferably includes a lower member and an upper member which are hinged together to form a boxlike enclosure that can be swung open and closed. The members are preferably made of plastic, such as injection molded plastic. A suitable enclosure is available from Bell Laboratories of Madison, Wis. and sold under the product name "Protecta Jr. Bait Station". This enclosure is 6"×5½" and 3" high, and has a durable hinge connecting the upper member and the lower member and includes a screw lock to secure the enclosure in a closed condition so that children or larger animals are not able to open the enclosure and reach the contents thereof.

In a preferred embodiment, the applicator comprising a flexible material is attached to the upper member with a portion thereof hanging into the enclosure such that when a rodent enters and moves through the chamber, the fibrous strands of the applicator rub across the fur or skin of the rodent and apply a small amount of the composition thereon to the skin or fur of the rodent. The flexible material may be strands a fibrous material, such as strands of cotton wick.

The following nonlimiting examples serve to further illustrate the present invention.

EXAMPLE 1

A Protecta Jr. (Bell Laboratories, Madison, Wis.) mouse bait box is modified as follows: a cotton yarn wick is stapled to the underside of the lid just in front of the feeding area entry; two adsorbent nylon strips are affixed to the outer edges of the food block trays. Two to three ml. of an oil-based composition comprising 3-cyano-1-(2,6-dichloro-4-trifluoromethyl)phenyl-5-N-(ethoxyacetyl)-N-methyl-4-trifluoromethylsulfinylpyrozole (0.1% to 5.0%, w/w) is applied to the wick and strip, and the lid is closed and locked with a set screw.

Five to thirty modified bait boxes are set out per hectare of property where mice are expected to be. Boxes are rebaited and wicks and strips replenished at 4 week intervals from April through August. Rodents entering the boxes come into contact with the wicks and/or strips containing the ectoparasiticide resulting in long-term control of Arthropods, especially ticks.

We claim:

1. A method of controlling ticks in small rodents comprising providing one or more enclosures of appropriate size to said rodents, said enclosures having one or more peripheral openings allowing entry and egress of rodents therein, said enclosure including at least one applicator arranged to contact rodents that enter said enclosure, providing a composition consisting essentially of an ectoparasiticide and inactive ingredients on said applicator, and placing said one or more enclosures in a locus at which said rodents are expected; said applicator being arranged and said composition being provided to apply an ectoparasiticidally effective amount of the composition to the skin or hair of said rodents upon contact with said applicator, wherein the applicator is inaccessible to contact with a human hand from said one or more peripheral openings and further wherein the ectoparasiticide is a compound of formula:

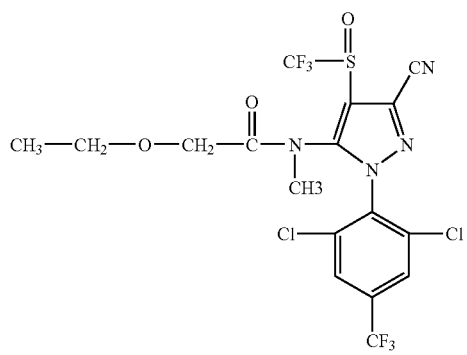

also known as 3-cyano-1-(2,6-dichloro-4-trifluoromethyl)phenyl-5-N-(ethoxyacetyl)-N-methyl-4-trifluoromethylsulfinylpyrazole, said ectoparasiticide being present in said composition in an amount of from 0.1% to 5% by weight and present in said one or more enclosures in an amount of from 0.001 gram to 2.0 grams per enclosure.

2. The method according to claim 1 wherein the rodent is a mouse, rat, vole, chipmunk or squirrel.

3. The method according to claim 1 wherein the ticks are of the genus $Ixodes$.

4. The method according to claim 1 wherein the composition is hydrophobic.

5. The method of claim 1 wherein the amount of ectoparasiticide is from 0.100 g per enclosure to 2.0 g per enclosure.

6. The method according to claim 1 wherein the percent by weight of the ectoparasiticide in the composition is from 0.25% to 1%.

7. The method according to claim 1 wherein the device further comprises a foodstuff for the rodent.

8. The method according to claim 1 wherein from one to ten enclosures are placed per hectare of locus.

9. The method according to claim 1 wherein the enclosure further defines a passageway through which a rodent is attracted to proceed.

10. The method according to claim 9 wherein the applicator is disposed in the passageway.

11. The method according to claim 1 wherein the applicator is disposed adjacent to or near one of the one or more peripheral openings.

12. The method according to claim 1 wherein the applicator is rechargeable from the outside of the enclosure without necessity to open the enclosure.

13. The method according to claim 1 wherein the applicator is replaceable.

14. The method according to claim 1 wherein the applicator is a small mop head.

15. The method according to claim 1 wherein the applicator is a brush.

16. The method of claim 1 wherein from 1–50 enclosures are placed per hectare of locus.

17. A method for reducing the transmission of diseases by ticks comprising providing one or more enclosures of appropriate size for small rodents, said enclosures having one or more peripheral openings allowing entry and egress of rodents therein, said enclosure including at least one applicator arranged to contact rodents that enter said enclosure; providing a composition consisting essentially of an ectoparasiticide having the formula:

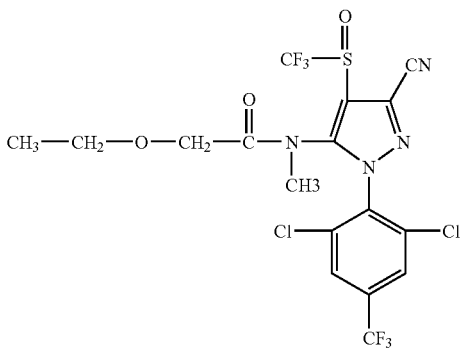

also known as 3-cyano-1-(2,6-dichloro-4-trifluoromethyl) phenyl-5-N-(ethoxyacetyl)-N-methyl-4-trifluoromethyl-sulfinylpyrazole, which is present in said composition in an amount of from 0.1% to 5% by weight and present in said one or more enclosures in an amount of from 0.001 gram to 2.0 grams per enclosure, and inactive ingredients, on said applicator, and placing said one or more enclosures in a locus at which said rodents are expected; said applicator being arranged and said composition being provided to apply an ectoparasiticidally effective amount of ectoparasiticide to the skin or hair of said rodents upon contact with said applicator, and wherein said applicator is inaccessible to contact with a human hand from said one or more peripheral openings.

18. The method of claim 17, wherein the percent by weight of the ectoparasiticide in the composition is from 0.25% to 1%.

19. The method of claim 17 wherein the amount of ectoparasiticide is from 0.100 g per enclosure to 2.0 g per enclosure.

20. The method of claim 17 wherein from 1–50 enclosures are placed per hectare of locus.

21. The method of claim 17 wherein from 1–10 enclosures are placed per hectare of locus.

22. A method of controlling ticks in small rodents comprising providing one or more enclosures of appropriate size to said rodents, said enclosures having one or more peripheral openings allowing entry and egress of rodents therein, said enclosure including at least one applicator arranged to contact rodents that enter said enclosure; providing a composition consisting essentially of an ectoparasiticide and inactive ingredients on said applicator, and placing said one or more enclosures in a locus at which said rodents are expected; said applicator being arranged and said composition being provided to apply an ectoparasiticidally effective amount of the composition to the skin or hair of said rodents upon contact with said applicator, wherein the applicator is inaccessible to contact with a human hand from said one or more peripheral openings and further wherein the ectoparasiticide is a veterinarily acceptable salt of a compound of formula:

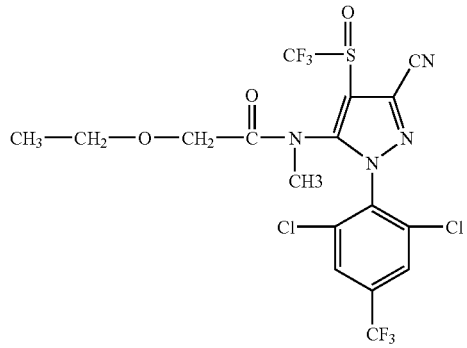

also known as 3-cyano-1-(2,6-dichloro-4-trifluoromethyl) phenyl-5-N-(ethoxyacetyl)-N-methyl-4-trifluoromethyl-sulfinylpyrazole, said ectoparasiticide being present in said composition in an amount of from 0.1% to 5% by weight and present in said one or more enclosures in an amount of from 0.001 gram to 2.0 grams per enclosure.

* * * * *

UNITED STATES PATENT AND TRADEMARK OFFICE
CERTIFICATE OF CORRECTION

PATENT NO. : 7,166,294 B2  Page 1 of 1
APPLICATION NO. : 10/282984
DATED : January 23, 2007
INVENTOR(S) : Gary O. Maupin et al.

It is certified that error appears in the above-identified patent and that said Letters Patent is hereby corrected as shown below:

Title Page;
    Item (56), References Cited, Other Publications, should include

-- J.S. Hunter et al.; "A comparison of the tick efficacy of Frontline Spray Treatment against the American Dog Tick and Brown Dog Tick"; Abstract, Proc. Am. Assoc. Vet. Parasitol. (41 Meet., 51, 1996) --.

Signed and Sealed this

Third Day of July, 2007

JON W. DUDAS
*Director of the United States Patent and Trademark Office*